United States Patent [19]
Dali

[11] 3,986,497
[45] Oct. 19, 1976

[54] ELECTRODE WIRE CLAMP

[75] Inventor: Carmelo Dali, Cheshire, Conn.

[73] Assignee: American Home Products Corporation, New York, N.Y.

[22] Filed: Apr. 28, 1975

[21] Appl. No.: 571,934

[52] U.S. Cl. .................. 128/2.06 E; 128/DIG. 4; 24/155 BB; 339/101
[51] Int. Cl.² ......................................... A61B 5/04
[58] Field of Search ............ 128/2.06 E, 2.1 E, 340, 128/346, 348, 404, 418, DIG. 4; 339/101, 108 R, 108 TP, 110 R, 110 C, 124, 228, 252 R, 252 S, 260, 261; 24/155 BB, 255 FC, 259 FC, 261 C

[56] References Cited
UNITED STATES PATENTS

| | | | |
|---|---|---|---|
| 1,005,283 | 10/1911 | Neher | 24/155 BB |
| 1,879,991 | 9/1932 | Pratt | 24/155 BB |
| 2,653,367 | 9/1953 | Orchoff | 24/155 BB |
| 3,261,357 | 7/1966 | Roberts et al. | 128/348 |
| 3,827,428 | 8/1974 | Hon et al. | 128/2.06 E |
| 3,831,589 | 8/1974 | Derring et al. | 128/2.1 E |
| 3,910,271 | 10/1975 | Neward | 128/2.06 E |

*Primary Examiner*—Robert W. Michell
*Assistant Examiner*—Lee S. Cohen
*Attorney, Agent, or Firm*—Darby & Darby

[57] ABSTRACT

An electrode wire clamp formed from a single piece of resilient material for affixation to one end of a tube having a wire running through it from an electrode affixed to the tube's other end, the wire being releasably held in fixed axial relationship to the tube by the clamp.

12 Claims, 5 Drawing Figures

U.S. Patent     Oct. 19, 1976     3,986,497
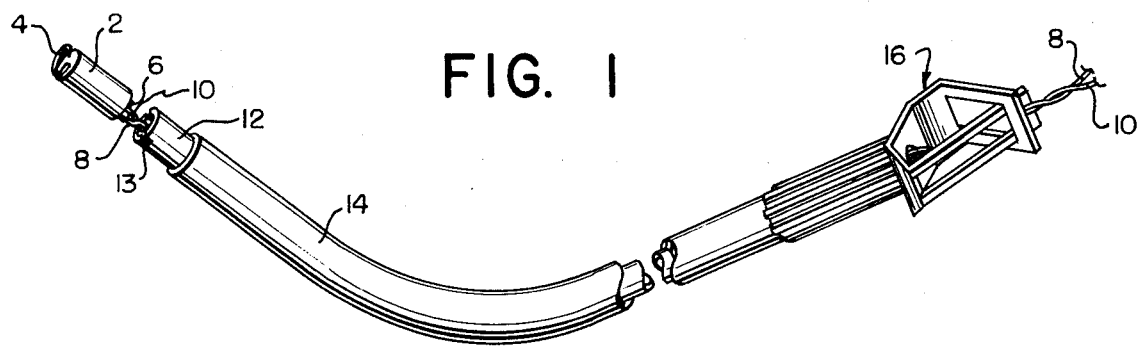
FIG. 1
FIG. 2
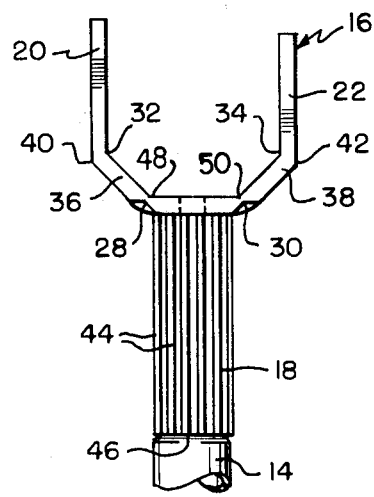
FIG. 3
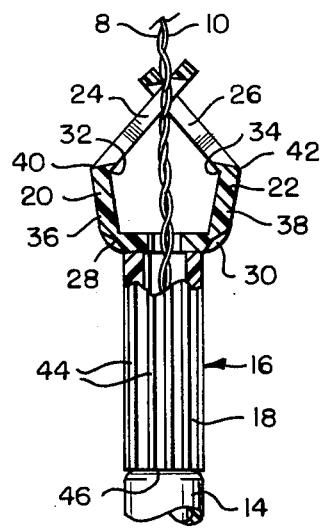
FIG. 4
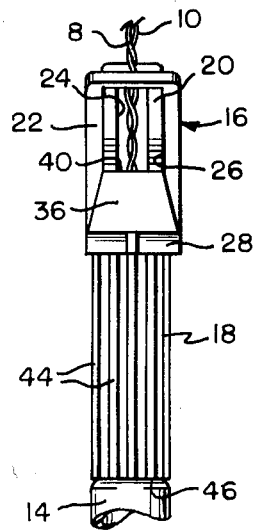
FIG. 5
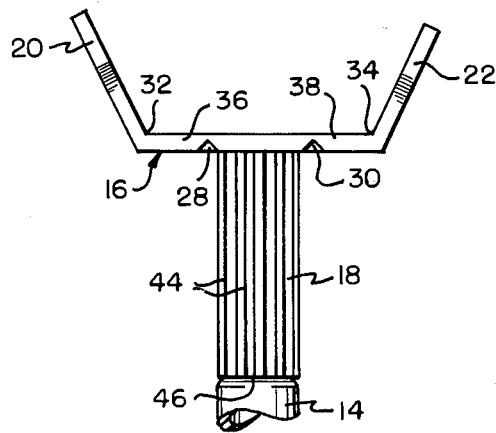

ELECTRODE WIRE CLAMP

BACKGROUND OF THE INVENTION

Devices are known which may be used to facilitate implantation of an electrode on an organ or fetus within a living body. In such devices, one example of which is shown in U.S. Pat. No. 3,827,428 to Hon et al. for "Bipolar Electrode Structure for Monitoring Fetal Heartbeat and the Like," the electrode structure is placed in abutment with the end of a driver tube, the electrode wires being passed through and clamped to the opposite end of the tube. The tube is inserted through an orifice in the body, sometimes aided by a guide tube as in Hon. After the electrode has been attached to the organ or fetus, the wire holding clamp is released permitting the driver tube to be withdrawn leaving the electrode in place with the electrode wires extending therefrom through the body orifice for connection to an electrical device.

Electrode wire clamps are known wherein the external end of the wire is held in fixed axial relationship to the driver tube by wrapping the wire about the clamp and/or forcing the wire through a narrow groove or slot where it is held in place. Such clamps are disadvantageous in that the tolerances associated with the clamps and with the wire and insulation thicknesses may cause the wires to be held so loosely as to permit axial movement relative to the driver tube, or too firmly to "give" under extreme tension which, when inadvertently applied, can rip the electrode from the organ or fetus thereby causing injury to it.

Another type of clamp is known wherein the wires are passed through an opening in the clamp, the opening being covered by a resiliently mounted apertured member which is pivoted to temporarily position the aperture of the member in axial alignment with the opening as the wires are passed through the clamp. When released, this member again covers the opening and pinches the wires to hold them within the driver tube, the aperture being forced out of alignment with the opening. Although this type of clamp is more likely to give when the wires are pulled hard enough to exert potentially injurious tension, it suffers from two principal disadvantages. First, it must be constructed from several components which, after formation, must be assembled. This adds to the expense of the device. Furthermore, should the clamp be grasped so as to prevent movement of the resilient member which holds the wires in place, the clamp will not release under pulling tension and thus is subject to the disadvantage of potential injury attributable to the groove and notch type devices hereinbefore described.

SUMMARY OF THE INVENTION

The object of this invention is to provide an inexpensive electrode wire clamp which can be used to secure firmly the wires of a fetal electrode of the type disclosed in U.S. Pat. No. 3,827,428, yet which will release the wires automatically when a pulling force is applied to the clamp sufficient to rip the electrode from the fetus.

Briefly, an electrode wire clamp according to the invention is formed from a single piece of resilient material generally formed in the shape of a Y, the central leg of the Y being tubular in shape and the arms of the Y being apertured so that they may be criss-crossed with one arm disposed through the other to form an opening in axial alignment with the tubular portion, the resilient arms serving to clamp wires passed through the opening and the tubular leg.

DESCRIPTION OF THE DRAWINGS

FIG. 1 is a perspective view of a fetal electrode probe utilizing an electrode wire clamp according to the invention;

FIG. 2 is a front elevation of a first embodiment of an electrode wire clamp according to the invention;

FIG. 3 is a front elevation, partially in section, of the electrode wire clamp of FIG. 2 in a wire grasping position;

FIG. 4 is a side elevation of the electrode wire clamp in a wire grasping position; and FIG. 5 is a front elevation of a second embodiment of the invention.

DESCRIPTION OF THE PREFERRED EMBODIMENT

Referring now to FIG. 1, an electrode assembly of the type disclosed in U.S. Pat. No. 3,827,428 of Hon et al. entitled "Bi-Polar Electrode Structure for Monitoring Fetal Heartbeat and the Like" comprises a cylindrical holder 2 made of an insulating material which supports a coil-like electrode 4 and a rear fin-like electrode 6. wires 8 and 10 are connected to respective electrodes 4 and 6 and pass through a flexible driver tube 12 having slots 13 which releaseably engage the fin-like electrode 6. Driver tube 12 can thus be used to push the electrode structure through the vaginal canal and turn it to engage the sharp coil-like electrode 4 within the tissue of a fetus contained therein. A curved guide tube 14 is provided to assist in passing the electrode structure and driver tube 12 through the vaginal canal and to prevent the electrode 4 from snagging intermediate body tissue before it has reached the intended point of engagement. The construction, purpose and method of this probe is explained in greater detail in U.S. Pat. No. 3,827,428.

After the electrode 4 is secured, the guide tube 14 and driver tube 12 are removed leaving the electrode structure in place within the body with the ends of wires 8 and 10 opposite those attached to electrodes 4 and 6 extending from the cervix for attachment to external electrical apparatus, e.g., a fetal heart monitor.

In order to maintain the rear electrode 6 within the slots 13 of driver tube 12 so that the electrode structure may be pushed through a body orifice and turned, the wires 8 and 10 are held in tension so that the holder 2 abuts against the forward end of driver tube 12. This is achieved by clamping wires 8 and 10, which are firmly secured within the holder 2, to the rear end of driver tube 12, thereby precluding separation of the holder 2 and the driver tube 12.

A first preferred embodiment of an electrode wire clamp 16 according to the invention is shown in FIG. 2. The clamp is generally Y-shaped having a central tubular leg 18 and respective first and second resilient arms 20 and 22.

Referring to FIGS. 3 and 4, the arms 20 and 22 are provided with respective rectangular apertures 24 and 26. The outer width of the arm 20 is less than the inner width of the arm 22 measured across the rectangular structure 26 and the sum of the lengths of the arms is greater than the distance between the arms so that the arm 20 may be passed through the aperture 26 in the arm 22. As shown the arms are divided into upper and lower portions and only the sum of the lengths of the upper portions need be greater than the distance between the upper portions to allow the intended function.

The clamp 16 can be formed from a single piece of resilient material such as any resilient plastic or metal. Polyethylene is one material from which the electrode wire clamp 16 may be suitably fabricated. An injection molding process may be used to form the clamp from the resilient material. The clamp may also be assembled from several parts each manufactured by extrusion.

Desirably the electrode wire clamp 16 is formed with arms 20 and 22 in parallel relationship as shown in FIG. 2, or in divergent relationship as shown in a second preferred embodiment in FIG. 5. The inherent resiliency of the material from which the clamp 16 is formed should be such that when arms 20 and 22 are criss-crossed, with arm 20 inserted through the aperture 26 of arm 22, the arms are urged toward the non-intersecting position in which they were originally formed.

When the arms 20 and 22 are criss-crossed as shown in FIGS. 3 and 4 the wires 8 and 10 can be passed through the hollow tubular leg 18 and through respective apertures 24 and 26 of arms 20 and 22. After the resilient arms 20 and 22 are released they are urged into pinching relationship with the wires 8 and 10, the wires 8 and 10 preventing the arms 20 and 22 from assuming their original non-intersecting position. The pinching force applied by the arms 20 and 22 to the wires 8 and 10 should be sufficient to maintain the wires 8 and 10 under slight tension so that the electrode 6 is held within slots 13 of driver tube 12.

The clamp 16 is formed with grooves at 28 and 30 and preformed bends at 32 and 34. Alternatively, the clamp may be formed as shown in FIG. 5 with lower portions 36 and 38 of the arms 20 and 22 coplanar. It has been found, however, that by forming the clamp as shown in FIG. 2 with the lower portions 36 and 38 of arms 20 and 22 respectively pre-bent at 48 and 50 about the grooves 28 and 30 in angular relationship with one another, relief of substantial stress where the periphery of the tube 18 meets the arms 20 and 22 is possible while maintaining sufficient resiliency to clamp the wires 8 and 10 in place.

To remove clamp 16 and driver tube 12 to which it is affixed after engagement of electrode 4 in the fetus, the clamp 16 is squeezed at points 40 and 42 thereby relieving the tension of arms 20 and 22 on the wires 8 and 10. Besides providing a facile means of releasing the clamp, this design has inherent in it a safety feature whereby when the clamp 16 is inadvertently grasped and pulled there is a tendency to apply pressure to points 40 and 42 thus loosening the clamp 16 and preventing the electrode 4 from being ripped from the organ or fetus to which it is affixed. When it is desired to manipulate the clamp and driver tube arrangement without loosening the clamp 16, the clamp 16 may be lightly grasped at points 40 and 42 with pressure insufficient to cause it to release the wires 8 and 10, or the clamp 16 may be grasped lower down about the tubular portion 18. The circumference of the tubular portion 18 may be provided with longitudinal ribs 44 to facilitate rotation of the clamp 16, driver tube 12, and the electrode structure for engagement of the spiral electrode 4 in the body tissue.

The lower end 46 of the tubular portion 18 may be forced over or into the driver tube 12, the resiliency of the material from which the clamp 16 is fabricated enabling a forced fit sufficient to prevent both axial and rotatonal movement between the clamp 16 and driver tube 12.

What is claimed is:

1. An electrode wire clamp comprising a generally Y-shaped member having a central tubular leg open at both of its ends and first and second resilient arms, having mutually facing respective apertures, extending from said leg, the transverse inner dimension of the first apertured arm being greater than the transverse outer dimension of the second apertured arm with the sum of the lengths of the arms being greater than the distance between the arms so that said arms may be bent into intersecting relationship with said second arm passing through the aperture in said first arm and the axis of said leg passing through both apertures, said arms being resiliently urged toward their original non-intersecting position.

2. An electrode wire clamp according to claim 1 wherein said apertures are rectangular in shape.

3. An electrode wire clamp according to claim 1 wherein said arms are provided with transverse grooves adjacent their intersection with said leg to facilitate bending.

4. An electrode wire clamp according to claim 1 wherein said arms are formed with bends dividing each arm into respective upper and lower portions with the lower portions connecting the respective upper portions to said tubular leg and the sum of the lengths of the upper portions being greater than the distance between the upper portions.

5. An electrode wire clamp according to claim 4 wherein said lower portions are normally coplanar and transverse to said leg axis.

6. An electrode wire clamp according to claim 4 wherein said upper portions are normally parallel.

7. An improved device for monitoring electrical activity within a living body including an electrode structure adapted for implanting inside a body cavity, a wire connected at one end to the electrode structure with its other end adapted to extend from the cavity, a driver tube having open front and rear ends with the front end separably engaging said electrode structure, said wire passing through said driver tube and extending from and clamped under tension to the rear end of said driver tube to maintain the electrode structure in abutting relationship with the forward end of the driver tube, wherein the improvement comprises an electrode wire clamp affixed to said rear end of said driver tube, said clamp being Y-shaped and having a central tubular leg open at both of its ends and first and second resilient arms, having mutually facing apertures, extending from said leg, the leg being affixed to said driver tube at the end opposite the arms, the transverse inner dimension of the first apertured arm being greater than the transverse outer dimension of the second apertured arm with the sum of the lengths of the arms being greater than the distance between the arms so that said arms may be bent into intersecting relationship, with said second arm passing through the aperture in said first arm and said wire passing through both apertures and said tubular leg, said arms being resiliently biased to releasably grasp said wire.

8. Apparatus according to claim 7 wherein said apertures are rectangular in shape.

9. Apparatus according to claim 7 wherein said arms are provided with transverse grooves adjacent their intersection with said leg to promote bending.

10. Apparatus according to claim 7 wherein said arms are formed with bends dividing each arm into respective lower and upper portions with the lower portions connecting the respective upper portions to said tubular leg and the sum of the lengths of the upper portions being greater than the distance between the upper portions.

11. Apparatus according to claim 10 wherein said lower portions are normally coplanar and transverse to the axis of said tubular leg.

12. Apparatus according to claim 10 wherein said upper portions are normally parallel.

* * * * *